(12) United States Patent
Christoph et al.

(10) Patent No.: US 7,361,690 B2
(45) Date of Patent: Apr. 22, 2008

(54) COMPOSITIONS AND METHODS FOR THE TREATMENT OF URINARY INCONTINENCE

(75) Inventors: Thomas Christoph, Aachen (DE); Elmar Friderichs, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 124 days.

(21) Appl. No.: 10/978,565

(22) Filed: Nov. 2, 2004

(65) Prior Publication Data

US 2005/0065120 A1  Mar. 24, 2005

Related U.S. Application Data

(60) Division of application No. 10/448,443, filed on May 30, 2003, now abandoned, which is a continuation of application No. PCT/EP01/13917, filed on Nov. 28, 2001.

(30) Foreign Application Priority Data

Nov. 30, 2000   (DE)   ................ 100 59 413

(51) Int. Cl.
    *A61K 31/135*   (2006.01)
(52) U.S. Cl. .................................... 514/646
(58) Field of Classification Search ................ 514/646
    See application file for complete search history.

(56) References Cited

U.S. PATENT DOCUMENTS

| 4,371,720 | A | 2/1983 | Johnson et al. | |
| 5,733,936 | A | 3/1998 | Buschmann et al. | |
| 5,811,582 | A | 9/1998 | Buschmann et al. | |
| 6,090,856 | A * | 7/2000 | Sasaki | 514/646 |
| 6,593,373 | B2 * | 7/2003 | Koegel et al. | 514/646 |
| 6,660,774 | B2 * | 12/2003 | Christoph et al. | 514/646 |
| 6,908,944 | B2 * | 6/2005 | Christoph et al. | 514/469 |

FOREIGN PATENT DOCUMENTS

| DE | 19525137 | 1/1997 |
| DE | 10004926 | 8/2001 |
| EP | 1005861 | 6/2000 |

OTHER PUBLICATIONS

Chutka et al., "Urinary Incontinence in the Elderly", *Drugs*, vol. 56, No. 4 (1998), pp. 587-595.

* cited by examiner

*Primary Examiner*—Kevin E. Weddington
(74) *Attorney, Agent, or Firm*—Crowell & Moring LLP

(57) ABSTRACT

A method for treating increased uninary urgency or urinary incontinence, comprising administering an effective amount of a compound corresponding to formula I

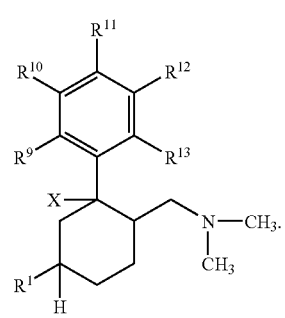

It has been surprisingly discovered that the methods of the present invention are effective for treating increased urinary urgency or urinary incontinence. Also disclosed are methods of treatment using related pharmaceutical compositions.

8 Claims, No Drawings

COMPOSITIONS AND METHODS FOR THE TREATMENT OF URINARY INCONTINENCE

CROSS REFERENCE TO RELATED APPLICATIONS

The present application is a division of U.S. patent application Ser. No. 10/448,443, filed May 30, 2003, which is a continuation of International Patent Application No. PCT/EP01/13917, filed Nov. 28, 2001, designating the United States of America and published in German as WO 02/43714 A2, the entire disclosure of which is incorporated herein by reference. Priority is claimed based on Federal Republic of Germany Patent Application No. 100 59 413.1, filed Nov. 30, 2000.

FIELD OF THE INVENTION

The present invention relates to the use of substituted 6-dimethylaminomethyl-1-phenylcyclohexane compounds as free bases and/or in the form of physiologically compatible salts for the production of a medicament for treating increased urinary urgency or urinary incontinence, as well as corresponding medicaments and methods for treating increased urinary urgency or urinary incontinence.

BACKGROUND OF THE INVENTION

Urinary incontinence is the involuntary passing of urine. This occurs in an uncontrolled manner if the pressure within the bladder exceeds the pressure required to close the ureter. Causes may include on the one hand an increased internal bladder pressure (e.g. due to detrusor instability) resulting in urgency incontinence, and on the other hand a reduced sphincter pressure (e.g. after childbirth or surgical intervention) resulting in stress incontinence. The detrusor is the collection of coarse bundles forming the multilayered muscular wall of the bladder, whose contraction leads to the discharge of urine, and the sphincter is the constrictor muscle of the urethra. Mixed forms of these types of incontinence as well as so-called overflow incontinence (e.g. in the case of benign prostatic hyperplasia) or reflex incontinence (e.g. following damage to the spinal cord) occur. Further details may be found in Chutka, D. S. and Takahashi P. Y., 1998, Drugs 560: 587-595.

Urinary urgency is the state of increased bladder muscle tension ending in urine discharge (micturition) when the bladder is almost full (or when its capacity is exceeded). This muscle tension acts as a stimulus to urination. Increased urinary urgency is understood in this connection to mean in particular the occurrence of premature or more frequent and sometimes even painful urinary urgency up to so-called dysuria. This consequently leads to a significantly increased frequency of micturition. The causes may include, inter alia, inflammation of the bladder and neurogenic bladder disorders, as well as bladder tuberculosis. However, all causes have not yet been elucidated.

Increased urinary urgency and also urinary incontinence are regarded as extremely unpleasant and there is therefore a clear need to achieve the greatest possible long-term improvement in patients affected by these medical conditions.

Increased urinary urgency and in particular urinary incontinence are normally treated with substances that act on the reflexes of the lower urinary tract (Wein A. J., 1998, Urology 51 (Suppl. 21): 43-47). In general these are medicaments that have an inhibiting effect on the detrusor muscle, which is responsible for the internal bladder pressure. These medicaments include parasympatholytics such as oxybutynin, propiverine or tolterodine, tricyclic antidepressants such as imipramine, or muscle relaxants such as flavoxate. Other medicaments that in particular increase the resistance of the urethra or cervix of the bladder have affinities to α-adrenoreceptors such as ephedrine, to β-adrenoreceptors such as clenbutarol, or are hormones such as estradiol. Also, certain opioids, diarylmethylpiperazines and diarylmethylpiperidines have been described for this medical condition in WO 93/15062.

It should be noted that the treatment of the above generally involves a long-term use of medicaments. In contrast to many other situations in which analgesics are used, patients suffering from urinary incontinence are subjected to very unpleasant but not intolerable discomfort. Accordingly, even more so than with analgesics, care should be taken to avoid side effects if the patient does not wish to exchange one discomfort for another. Furthermore, in the long-term treatment of urinary incontinence analgesic effects are also largely undesirable.

DESCRIPTION OF THE INVENTION

The object of the present invention is accordingly to find substances that are helpful in the treatment of increased urinary urgency or urinary incontinence and that at effective doses preferably at the same time exhibit fewer side effects and/or analgesic effects than are known from the prior art.

It has now surprisingly been found that compounds according to the general formula I have an outstanding effect on bladder function and accordingly are suitable for treating corresponding medical conditions.

Accordingly, the present invention provides for the use of a substituted 6-dimethylaminomethyl-1-phenylcyclohexane compound according to the general formula I

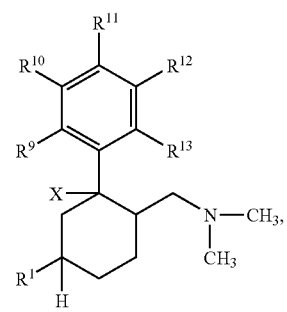

wherein
  X is selected from OH, F, Cl, H or OC(O)$R^7$ where $R^7$ is selected from $C_{1-3}$-alkyl that is branched or unbranched, saturated or unsaturated, unsubstituted or singly or multiply substituted,
  $R^1$ is selected from $C_{1-4}$-alkyl, benzyl, $CF_3$, OH, $OCH_2$—$C_6H_5$, O-$C_{1-4}$-alkyl, Cl or F and
  $R^9$ to $R^{13}$ are in each case selected independently of one another from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl that is branched or unbranched, saturated or unsaturated, unsubstituted or singly or multiply substituted; phenyl that is unsubstituted or singly or multiply substituted;

where $R^{14}$ is selected from $C_{1-6}$-alkyl; pyridyl, thienyl, thiazolyl, phenyl, benzyl or phenethyl, in each case unsubstituted or singly or multiply substituted; PO(O—$C_{1-4}$-alkyl)$_2$, CO(OC$_{1-5}$-alkyl), CONH—$C_6H_4$—($C_{1-3}$-alkyl), CO($C_{1-5}$-alkyl), CO—CHR$^{17}$—NHR$^{18}$, CO—$C_6H_4$—R$^{15}$, where $R^{15}$ is ortho-OCOC$_{1-3}$-alkyl or meta- or para-CH$_2$N(R$^{16}$)$_2$ where $R^{16}$ is $C_{1-4}$-alkyl or 4-morpholino, wherein in the radicals $R^{14}$, $R^{15}$ and $R^{16}$ the alkyl groups may be branched or unbranched, saturated or unsaturated, unsubstituted or singly or multiply substituted;

where $R^{17}$ and $R^{18}$ are in each case selected independently of one another from H; $C_{1-6}$-alkyl that is branched or unbranched, saturated or unsaturated, unsubstituted or singly or multiply substituted; phenyl, benzyl or phenethyl that is in each case unsubstituted or singly or multiply substituted, or $R^9$ and $R^{10}$ or $R^{10}$ and $R^{11}$ together form an OCH$_2$O, OCH$_2$CH$_2$O, OCH=CH, CH=CHO, CH=C(CH$_3$)O, OC(CH$_3$)=CH, (CH$_2$)$_4$ or OCH=CHO ring, in the form of their racemates; enantiomers, diastereomers, in particular mixtures of their enantiomers or diastereomers, or an individual enantiomer or diastereomer; their bases and/or salts of physiologically compatible acids for the production of a medicament for treating increased urinary urgency or urinary incontinence.

It has surprisingly been found that the aforementioned substances have a significant positive influence on certain physiological parameters that are of importance in increased urinary urgency or urinary incontinence, and thus have a positive influence either on the threshold pressure, the intercontraction interval, or on reducing the rhythmic bladder contractions and/or bladder capacity. Each one of these changes can mean a significant improvement in the range of symptoms exhibited by affected patients. Corresponding compounds and their production are known from DE 195 25 137 A1, the content of which is incorporated herein in its entirety.

Within the context of the present invention alkyl radicals are understood to be saturated or unsaturated, branched or unbranched hydrocarbons that may also be unsubstituted or at least singly substituted. Preferred alkyl radicals are methyl, ethyl, vinyl (ethenyl), propyl, allyl (2-propenyl), 1-propinyl, methylethyl, n-butyl, sec.-butyl, tert.-butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, CHF$_2$, CF$_3$ or CH$_2$OH.

Furthermore, cycloalkyl radicals within the context of this invention are understood to be saturated cyclic hydrocarbons that may also be at least singly substituted. Preferred cycloalkyl radicals are cyclopropyl, cyclobutyl, cyclopentyl, cyclohexyl or cycloheptyl.

In connection with alkyl and cycloalkyl, the term substituted within the context of this invention is understood to mean the replacement of an hydrogen atom by F, Cl, Br, I, NH$_2$, SH or OH, and "multiply substituted" is understood to mean that the substitution takes place on different as well as on the same atoms with the same or different substituents, for example triply on the same C atom as in the case of CF$_3$, or at different positions as in the case of —CH(OH)—CH=CH=CHCl$_2$.

In connection with phenyl, benzyl or phenethyl, the term substituted is preferably understood to mean substitution of H with F, Cl, Br, I, CH$_2$F, CHF$_2$, CF$_3$, OH, SH, OR$^{19}$, OCF$_3$, SR$^{19}$, NH$_2$, CONH$_2$, SOCH$_3$, SOCF$_3$, SO$_2$CH$_3$, SO$_2$CF$_3$, CN, COOR$^{19}$, NO$_2$; $C_{1-6}$-alkyl that is branched or unbranched, saturated or unsaturated, unsubstituted or singly or multiply substituted; or phenyl that is unsubstituted;

where $R^{19}$ is selected from $C_{1-6}$-alkyl that is branched or unbranched, saturated or unsaturated, unsubstituted or singly or multiply substituted; or $C_{3-7}$-cycloalkyl.

Suitable salts within the meaning of the present invention and in each of the claimed uses are salts of the respective active ingredient with inorganic or organic acids and/or a sugar substitute such as saccharine, cyclamate or acesulfam. However, the hydrochloride is particularly preferred.

In this connection it is preferred to use compounds according to formula I in which X is selected from OH, F, Cl, OC(O)CH$_3$ or H, preferably OH, F or H, in particular OH.

Furthermore, it is also preferred to use compounds according to formula I in which $R^1$ is selected from $C_{1-4}$-alkyl, CF$_3$, OH, O—$C_{1-4}$-alkyl, Cl or F, preferably OH, CF$_3$ or CH$_3$.

It is furthermore preferred to use compounds according to formula I in which $R^9$ to $R^{13}$, wherein three or four of the radicals $R^9$ to $R^{13}$ must correspond to H, are selected independently of one another from H, Cl, F, OH, CF$_2$H, CF$_3$ or $C_{1-4}$-alkyl that is saturated and unsubstituted, branched or unbranched; OR$^{14}$ or SR$^{14}$ where $R^{14}$ is selected from $C_{1-3}$-alkyl that is saturated and unsubstituted, branched or unbranched;

preferably H, Cl, F, OH, CF$_2$H, CF$_3$, OCH$_3$ or SCH$_3$ or $R^{12}$ and $R^{11}$ form a 3,4-OCH=CH ring in particular those in which, if $R^9$, $R^{11}$ and $R^{13}$ correspond to H, then one of $R^{10}$ or $R^{12}$ also corresponds to H, while the other is selected from:

Cl, F, OH, CF$_2$H, CF$_3$, OR$^{14}$ or SR$^{14}$, preferably OH, CF$_2$H, OCH$_3$ or SCH$_3$, or, if $R^9$ and $R^{13}$ correspond to H and $R^{11}$ corresponds to OH, OCH$_3$, Cl or F, preferably Cl, then one of $R^{10}$ or $R^{12}$ also corresponds to H, while the other corresponds to OH, OCH$_3$, Cl or F, preferably Cl, or, if $R^9$, $R^{10}$, $R^{12}$ and $R^{13}$ correspond to H, $R^{11}$ is selected from CF$_3$, CF$_2$H, Cl or F, preferably F, or, if $R^{10}$, $R^{11}$ and $R^{12}$ correspond to H, one of $R^9$ or $R^{13}$ also corresponds to H, while the other is selected from OH, OC$_2$H$_5$ or OC$_3$H$_7$.

Also preferred is the use of compounds according to formula I wherein $R^9$, $R^{11}$ and $R^{13}$ correspond to H, one of $R^{10}$ or $R^{12}$ also corresponds to H, while the other is selected from:

Cl, F, OH, SH, CF$_2$H, CF$_3$, OR$^{14}$ or SR$^{14}$, preferably OH or OR$^{14}$, in particular OH or OC$_{1-3}$-alkyl, preferably OH or OCH$_3$.

It is also preferred if compounds according to formula I in the form of the diastereomers with the relative configuration Ia

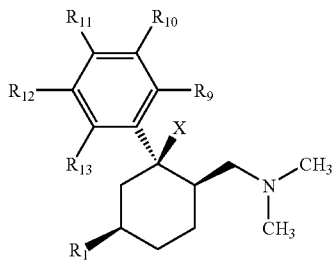

are present, in particular in mixtures with a higher proportion of this diastereomer compared to the other diastereomers or as pure diastereomer.

It is furthermore preferred if the compounds of the formula I are used in the form of the (+) enantiomer, in particular in mixtures with a higher proportion of the (+) enantiomer compared to the (−) enantiomer of a racemic compound or as pure (+) enantiomer.

In general, with the preferred use of the (+) enantiomer a smaller proportion of (−) enantiomer compared to the (+) enantiomer is also acceptable and may—but need not be—involved in the use according to the invention.

It is particularly preferred to use a compound selected from the following group:
- (1RS,3RS,6RS)-6-dimethylaminomethyl-1-(3-methoxyphenyl)-cyclohexane-1,3-diol,
- (+)-(1R,3R,6R)-6-dimethylaminomethyl-1-(3-methoxyphenyl)-cyclohexane-1,3-diol,
- (1RS,3RS,6RS)-6-dimethylaminomethyl-1-(3-hydroxyphenyl)-cyclohexane-1,3-diol,
- (1RS,3 SR,6RS)-6-dimethylaminomethyl-1-(3-methoxyphenyl)-cyclohexane-1,3-diol,
- (+)-(1R,3R,5S)-3-(2-dimethylaminomethyl-1-hydroxy-5-methylcyclohexyl)-phenol, and
- (1RS,2RS,5RS)-3-(2-dimethylaminomethyl-1-hydroxy-5-trifluoromethylcyclohexyl)-phenol, preferably as hydrochloride Also, if the uses according to the invention produce only slight side effects, it may for example also be advantageous in order to avoid certain types of dependence to use, in addition to compounds according to the general formula I, also morphine antagonists, in particular naloxone, naltrexone and/or levallorphan.

The invention also comprises medicaments for treating increased urinary urgency or urinary incontinence, which medicaments contain as active ingredient at least one substituted 6-dimethylaminomethyl-1-phenylcyclohexane compound according to the general formula I

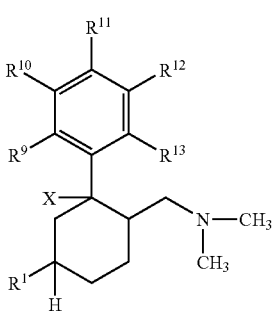

wherein
X is selected from OH, F, Cl, H or OC(O)$R^7$ where $R^7$ is selected from $C_{1-3}$-alkyl that is branched or unbranched, saturated or unsaturated, unsubstituted or singly or multiply substituted,
$R^1$ is selected from $C_{1-4}$-alkyl, benzyl, $CF_3$, OH, $OCH_2$—$C_6H_5$, O—$C_{1-4}$-alkyl, Cl or F and
$R^9$ to $R^{13}$ are in each case selected independently of one another from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl that is branched or unbranched, saturated or unsaturated, unsubstituted or singly or multiply substituted; phenyl that is unsubstituted or singly or multiply substituted;
where $R^{14}$ is selected from $C_{1-6}$-alkyl; pyridyl, thienyl, thiazolyl, phenyl, benzyl or phenethyl, in each case unsubstituted or singly or multiply substituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-$OCOC_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups may be branched or unbranched, saturated or unsaturated, unsubstituted or singly or multiply substituted;
where $R^{17}$ and $R^{18}$ are in each case selected independently of one another from H; $C_{1-6}$-alkyl that is branched or unbranched, saturated or unsaturated, unsubstituted or singly or multiply substituted; phenyl, benzyl or phenethyl that is in each case unsubstituted or singly or multiply substituted, or $R^9$ and $R^{10}$ or $R^{10}$ and $R^{11}$ together form an $OCH_2O$, $OCH_2CH_2O$, $OCH$═$CH$, $CH$═$CHO$, $CH$═$C(CH_3)O$, $OC(CH_3)$═$CH$, $(CH_2)_4$ or $OCH$═$CHO$ ring, in the form of their racemates; enantiomers, diastereomers, in particular mixtures of their enantiomers or diastereomers, or an individual enantiomer or diastereomer; their bases and/or salts of physiologically compatible acids as well as optionally at least one additive and/or auxiliary substance.

Suitable salts within the context of the present invention and in each of the claimed uses are salts of the respective active ingredient with inorganic or organic acids and/or a sugar substitute such as saccharine, cyclamate or acesulfam. However, the hydrochloride is particularly preferred.

Suitable additives and/or auxiliary substances within the context of the present invention are all substances known to the person skilled in the art from the prior art for achieving the preparation of galenical formulations. The choice of these auxiliary substances as well as the amounts thereof to be used depend on whether the medicament is to be administered orally, intravenously, intraperitoneally, intradermally, intramuscularly, intranasally, buccally or topically. For oral application preparations in the form of tablets, chewable tablets, sugar-coated pills, capsules, granules, drops, juices or syrups are suitable, while for parenteral, topical and inhalative application solutions, suspensions, readily reconstitutable dry preparations as well as sprays are suitable. A further possible form of application are suppositories for rectal use. The use in a depôt form, in dissolved form, in a carrier film or a plaster, optionally with the addition of agents promoting penetration of the skin, are examples of suitable percutaneous application forms. Examples of auxiliary substances and additives for oral application forms are disintegrants, lubricants, binders, fillers, mould release agents, optionally solvents, taste enhancers, sugars, in particular excipients, diluents, colorants, antioxidants, etc. For suppositories there may be used inter alia waxes or fatty acid esters, and for parenteral application agents there may be used excipients, preservatives, suspension auxiliaries, etc. The amounts of active ingredient to be administered to the patient vary depending on the patient's weight, on the type of application and the severity of the medical condition. The compounds according to the invention may be employed in delayed release form in preparations for oral, rectal or percutaneous use. Corresponding retard formulations or delayed-release formulations, in particular in the form of a "once daily" preparation that has to be taken only once a day, are particularly preferred for use in the medical condition covered by the invention.

Also preferred are medicaments that contain at least 0.05 to 90.0% of the active ingredient, in particular low effective dosages in order to avoid side effects or analgesic effects. Normally 0.1 to 5000 mg/kg, in particular 1 to 500 mg/kg and preferably 2 to 250 mg/kg body weight of at least one compound of formula I are administered. However, the administration of 0.01 to 5 mg/kg, preferably 0.03 to 2 mg/kg and in particular 0.05 to 1 mg/kg body weight is also preferred and customary.

Auxiliary substances may for example include the following: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatins, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, gum arabic, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soy bean oil, lecithin, sodium lactate, polyoxyethylene fatty acid esters and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The medicaments and pharmaceutical compositions according to the invention are produced with the aid of agents, equipment, methods and processes well known in the prior art for pharmaceutical formulations, such as are described in "Remington's Pharmaceutical Sciences", Editor A. R. Gennaro, 17$^{th}$ Edition, Mack Publishing Company, Easton, Pa. (1985), in particular in Part 8, Chapters 76 to 93.

Thus for example, for a solid formulation such as a tablet the active ingredient of the medicament, i.e. a compound of the general structure I or one of its pharmaceutically acceptable salts, may be granulated with a pharmaceutical carrier, for example conventional tablet constituents such as maize starch, lactose, sucrose, sorbitol, talcum, magnesium stearate, dicalcium phosphate or pharmaceutically acceptable gums, and pharmaceutical diluents, such as water, in order to form a solid composition that contains a compound according to the invention or a pharmaceutically acceptable salt thereof in homogeneous distribution. A homogeneous distribution is understood here to mean that the active ingredient is uniformly distributed over the whole composition so that the latter can be subdivided without any difficulty into equally effective unit dose forms such as tablets, pills or capsules. The solid composition is then subdivided into unit dose forms. The tablets or pills of the medicament according to the invention or of the compositions according to the invention may also be coated or compounded in another way in order to prepare a dose form with a delayed-release action. Suitable coating agents include polymeric acids and mixtures of polymeric acids with materials such as shellac, cetyl alcohol and/or cellulose acetate.

Also, if the medicaments according to the invention exhibit slight side effects it may be advantageous in order to avoid specific forms of dependence to use in addition to the compounds according to the general formula I also morphine antagonists, in particular naloxone, naltrexone and/or levallorphan.

Preferred are medicaments in which compounds according to general formula I are used, in which X is selected from
OH, F, Cl, OC(O)CH$_3$ or H, preferably OH, F or H, in particular OH.

Also preferred are medicaments in which compounds according to the general formula I are used in which R$^1$ is selected from
C$_{1-4}$-alkyl, CF$_3$, OH, O—C$_{1-4}$-alkyl, Cl or F, preferably OH, CF$_3$ or CH$_3$.

It is furthermore preferred if in the medicaments according to the invention compounds according to the general formula I are used in which R$^9$ to R$^{13}$, wherein three or four of the radicals R$^9$ to R$^{13}$ must correspond to H, are selected independently of one another from
H, Cl, F, OH, CF$_2$H, CF$_3$ or C$_{1-4}$-alkyl that is saturated and unsubstituted, branched or unbranched; OR$^{14}$ or SR$^{14}$ where R$^{14}$ is selected from C$_{1-3}$-alkyl that is saturated and unsubstituted, branched or unbranched;
preferably H, Cl, F, OH, CF$_2$H, CF$_3$, OCH$_3$ or SCH$_3$ or R$^{12}$ and R$^{11}$ form a 3,4-OCH═CH ring, in particular,
if R$^9$, R$^{11}$ and R$^{13}$ correspond to H, then one of R$^{10}$ or R$^{12}$ also corresponds to H, while the other is selected from:
Cl, F, OH, CF$_2$H, CF$_3$, OR$^{14}$ or SR$^{14}$, preferably OH, CF$_2$H, OR$^{14}$ or SCH$_3$, in particular OH or OC$_{1-3}$-alkyl, preferably OH or OCH$_3$, or,
if R$^9$ and R$^{13}$ correspond to H and R$^{11}$ corresponds to OH, OCH$_3$, Cl or F, preferably Cl, then one of R$^{10}$ or R$^{12}$ also corresponds to H, while the other corresponds to OH, OCH$_3$, Cl or F, preferably Cl, or,
if R$^9$, R$^{10}$, R$^{12}$ and R$^{13}$ correspond to H, R$^{11}$ is selected from CF$_3$, CF$_2$H, Cl or F, preferably F, or,
if R$^{10}$, R$^{11}$ and R$^{12}$ correspond to H, one of R$^9$ or R$^{13}$ also corresponds to H, while the other is selected from OH, OC$_2$H$_5$ or OC$_3$H$_7$.

Also preferred are medicaments in which compounds according to the general formula I are used, wherein R$^9$, R$^{11}$ and R$^{13}$ correspond to H, one of R$^{10}$ or R$^{12}$ also corresponds to H, while the other is selected from:
Cl, F, OH, SH, CF$_2$H, CF$_3$, OR$^{14}$ or SR$^{14}$, preferably OH or OR$^{14}$, in particular OH or OC$_{1-3}$-alkyl, preferably OH or OCH$_3$.

It is furthermore preferred if in the medicaments according to the invention compounds according to the general formula I are contained that are present in the form of the diastereomer with the relative configuration Ia

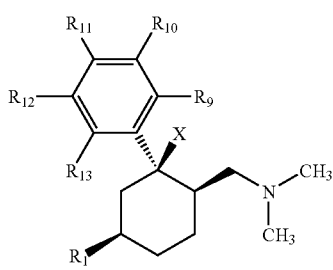

in particular in mixtures with a higher proportion of this diastereomer compared to the other diastereomers, or as pure diastereomer.

It is furthermore preferred if in the medicaments according to the invention compounds according to the general formula I are contained that are present in the form of the (+) enantiomer, in particular in mixtures with a higher proportion of the (+) enantiomer compared to the (−) enantiomer of a racemic compound or as pure (+) enantiomer.

Generally, with the preferred use of the (+) enantiomer a smaller proportion of (−) enantiomer compared to the (+) enantiomer is also acceptable and may—but need not—be contained in the medicaments according to the invention.

Particularly preferred are medicaments according to the invention that contain at least one compound selected from the following group:
(1RS,3RS,6RS)-6-dimethylaminomethyl-1-(3-methoxyphenyl)-cyclohexane-1,3-diol,
(+)-(1R,3R,6R)-6-dimethylaminomethyl-1-(3-methoxyphenyl)-cyclohexane-1,3-diol,
(1RS,3RS,6RS)-6-dimethylaminomethyl-1-(3 -hydroxyphenyl)-cyclohexane-1,3-diol,
(1RS,3SR,6RS)-6-dimethylaminomethyl-1-(3-methoxyphenyl)-cyclohexane-1,3-diol,
(+)-(1R,3R,5S)-3-(2-dimethylaminomethyl-1-hydroxy-5-methylcyclohexyl)-phenol, and
(1RS,2RS,5RS)-3-(2-dimethylaminomethyl-1-hydroxy-5-trifluoromethylcyclohexyl)-phenol preferably as hydrochloride.

The invention also provides a process for treating increased urinary urgency or urinary incontinence, in which the substituted 6-dimethylaminomethyl-1-phenylcyclohexane compounds according to the invention of the general formula I are used in the form of their racemates; enantiomers, diastereomers, in particular mixtures of their enantiomers or diastereomers, or in the form of an individual enantiomer or diastereomer; as free base and/or in the form of physiologically compatible salts.

The following examples serve to illustrate the invention without however restricting the subject matter of the invention.

EXAMPLES

Example 1

List of Tested Substances

The following is a list of the compounds tested as regards their effectiveness:

| Name | Cmpd. No. |
|---|---|
| (1RS,3RS,6RS)-6-dimethylaminomethyl-1-(3-methoxyphenyl)-cyclohexane-1,3-diol, hydrochloride | 24 |
| (+)-(1R,3R,6R)-6-dimethylaminomethyl-1-(3-methoxyphenyl)-cyclohexane-1,3-diol, hydrochloride | 25 |
| (1RS,3RS,6RS)-6-dimethylaminomethyl-1-(3-hydroxyphenyl)-cyclohexane-1,3-diol, hydrochloride | 26 |
| (1RS,3SR,6RS)-6-dimethylaminomethyl-1-(3-methoxyphenyl)-cyclohexane-1,3-diol, hydrochloride | 27 |
| (+)-(1R,2R,5S)-3-(2-dimethylaminomethyl-1-hydroxy-5-methylcyclohexyl)-phenol, hydrochloride | 28 |
| (1RS,2RS,5RS)-3-(2-dimethylaminomethyl-1-hydroxy-5-trifluoromethylcyclohexyl)-phenol,hydrochloride | 29 |

Example 2

Cystometry Tests on Conscious Fresh Rats

Cystometry investigations were carried out on fresh female Sprague-Dawley rats according to the method of Ishizuka et. al. ((1997), Naunyn-Schmiedeberg's Arch. Pharmacol. 355: 787-793). Three days after implantation of bladder and venous catheters the animals were investigated in the conscious state while freely moving. The bladder catheter was connected to a pressure gauge and an injection pump. The animals were placed in metabolic cages that enable the volume of urine to be measured. Physiological saline solution was infused (10 ml/hour) into the emptied bladder and the bladder pressure and volume of urine were continuously recorded. After a stabilization phase a 20-minute phase was recorded that was characterized by normal, reproducible micturition cycles. The following parameters among others were measured:

threshold pressure (TP), bladder pressure immediately before micturition, bladder capacity (BC), residual volume after prior micturition plus volume of infused solution during the filling phase, intercontraction interval (ICI), the time interval between consecutive micturition.

An increase in the threshold pressure (TP) indicates an important therapeutic effect in one of the medical conditions suitable for treatment with the method of the invention. Also, the intercontraction interval (ICI) is an important parameter for measuring the physiological effectiveness of a substance in the treatment of urinary incontinence, as is the bladder capacity (BC). In this connection, on account of the widely differing causes of the symptoms of these disease patterns it is not necessary to influence positively all three parameters in order for a medicament to be effective. It is therefore completely sufficient if a positive effect is demonstrated in only one of these parameters in order for the medicament to be of use in urinary incontinence or increased urinary urgency.

After recording three reproducible micturition cycles to provide a baseline value, the test substances 24 (1.0; 3.0; 5.0 mg/kg), 25 (1.5 mg/kg) and 26 (3.0 mg/kg) in a vehicle comprising 0.9% NaCl were applied intravenously and the effect on the cystometric parameters was recorded at 90 to 120 minutes. In the effect maximum the mean value of 3 micturition cycles was determined and recorded as a percentage change compared to the baseline value (Table 1).

TABLE 1

Effect on cystometric parameters of the test substances measured as changes compared to the baseline value

| Compound: (Concentration) | TP Threshold Pressure | BC Bladder Capacity | ICI Inter-Contraction Interval |
|---|---|---|---|
| 24 | | | |
| 1.0 mg/kg iv (n = 7) | +44.0%*** | −8.0% | −15%** |
| 3.0 mg/kg iv (n = 8) | +94.0%** | −16.0%* | −16%* |
| 5.0 mg/kg iv (n = 8) | +69.0%* | −26.0% | −21.2% |
| 25 | | | |
| 1.5 mg/kg iv (n = 8) | +62.0%* | −14.0%* | −9.0% |
| 26 | | | |
| 3.0 mg/kg iv (n = 7) | +86.0%*** | +29.0%*** | +27.0%* |

Note:
n corresponds to the number of experimental animals.

The investigated substances exhibit a positive effect on the bladder regulation and are therefore suitable for treating urinary incontinence.

Example 3

Cystometry Investigations in Narcotized Fresh Rats

The cystometric investigation was carried out on fresh female rats according to the method of Kimura et al. (Kimura et al., 1996, Int. J. Urol. 3: 218-227). The abdomen of narcotized ventilated rats is opened and the ureter is ligated. The urine is drawn off from the kidneys. A catheter is inserted into the bladder and secured in place. Saline is infused by means of an infusion pump via the catheter into the bladder until this exhibits rhythmic spontaneous activity in the form of contractions that can be recorded via a connected pressure recorder. The test substance is applied intravenously in a cumulative manner after stable starting values were reached. An effect on the bladder function is manifested by the suppression of the spontaneous contractions. The disappearance of the contractions over a period of 10 minutes serves as a parameter for their suppression.

With all the substances listed there was a measurable suppression of the spontaneous contractions in rats. Table 2 shows the mean value of the lowest dose from at least two experiments, in which contractions disappeared for the first time over a period of 10 minutes.

TABLE 2

Mean Value of Lowest Dose for Contraction Suppression

| Compound No. | Lowest Dose [mg/kg] |
|---|---|
| 27 | 115 (n = 2) |
| 28 | 16.7 (n = 3) |
| 29 | 23.3 (n = 3) |

Note:
n corresponds to the number of the experiments used to calculate the value.

The investigated substances exhibit a positive effect on bladder regulation and are thus suitable for treating urinary incontinence.

Example 4

Parenteral Application Form 1 g of the compound 26 is dissolved at room temperature in 1 l of water for injection purposes and is then adjusted to isotonic conditions by adding NaCl.

What is claimed is:

1. A method for treating increased urinary urgency or urinary incontinence, comprising administering to a subject in need thereof an effective amount of a compound selected from the group consisting of:

(1RS,3RS,6RS)-6-dimethylaminomethyl-1-(3-methoxyphenyl)-cyclohexane-1,3-diol, (+)-(1R,3R,6R)-6-dimethylaminomethyl-1-(3-methoxyphenyl)-cyclohexane-1,3-diol, (1RS,3RS,6RS)-6-dimethylaminomethyl-1-(3-hydroxyphenyl)-cyclohexane-1,3-diol, (1RS,3RS,6RS)-6-dimethylaminomethyl-1-(3-methoxyphenyl)-cyclohexane-1,3-diol, (+)-(1R,3R,5S)-3-(2-dimethylaminomethyl-1-hydroxy-5-methylcyclohexyl)-phenol, and (1RS,2RS,5RS)-3-(2-dimethylaminomethyl-1 -hydroxy-5-trifluoromethylcyclohexyl)-phenol or a salt thereof with a physiologically compatible acid.

2. A method according to claim 1, wherein said compound is provided in a pharmaceutical composition with a pharmaceutically acceptable excipient.

3. A method according to claim 1, wherein said compound is (1RS,3RS,6RS)-6-dimethylaminomethyl-1-(3-methoxyphenyl)-cyclohexane-1,3-diol or a hydrochloride thereof.

4. A method according to claim 1, wherein said compound is (+)-(1R,3R,6R)-6-dimethylaminomethyl-1-(3-methoxyphenyl)-cyclohexane-1,3-diol or a hydrochloride thereof.

5. A method according to claim 1, wherein said compound is (1RS,3RS,6RS)-6-dimethylaminomethyl-1-(3-hydroxyphenyl)-cyclohexane-1,3-diol or a hydrochloride thereof.

6. A method according to claim 1, wherein said compound is (1RS,3SR,6RS)-6-dimethylaminomethyl-1-(3-methoxyphenyl)-cyclohexane-1,3-diol or a hydrochloride thereof.

7. A method according to claim 1, wherein said compound is (+)-(1R,3R,5S)-3-(2-dimethylaminomethyl-1-hydroxy-5-methylcyclohexyl)-phenol or a hydrochloride thereof.

8. A method according to claim 1, wherein said compound is (1RS,2RS,5RS)-3-(2-dimethylaminomethyl-1 -hydroxy-5-trifluoromethylcyclohexyl)-phenol or a hydrochloride thereof.

* * * * *